(12) United States Patent
Warner et al.

(10) Patent No.: US 9,063,154 B2
(45) Date of Patent: *Jun. 23, 2015

(54) METHODS FOR MEASURING ANALYTE TRANSPORT ACROSS BARRIERS USING X-RAY FLUORESCENCE

(71) Applicant: XRpro Sciences, Inc., Los Alamos, NM (US)

(72) Inventors: Benjamin P. Warner, Los Alamos, NM (US); Rebecca L. E. Miller, Los Alamos, NM (US); Lori J. Peterson, Los Alamos, NM (US); Jennifer A. Berger, White Rock, NM (US); Eva R. Birnbaum, Los Alamos, NM (US)

(73) Assignee: Caldera Pharmaceuticals, Inc., Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/871,697

(22) Filed: Apr. 26, 2013

(65) Prior Publication Data

US 2013/0236887 A1 Sep. 12, 2013

Related U.S. Application Data

(62) Division of application No. 12/496,532, filed on Jul. 1, 2009, now Pat. No. 8,431,357.

(60) Provisional application No. 61/133,697, filed on Jul. 1, 2008, provisional application No. 61/208,115, filed on Feb. 20, 2009.

(51) Int. Cl.
| | |
|---|---|
| *C12Q 1/02* | (2006.01) |
| *G01N 21/76* | (2006.01) |
| *G01N 23/223* | (2006.01) |
| *G01N 33/50* | (2006.01) |
| *G01N 33/68* | (2006.01) |

(52) U.S. Cl.
CPC .......... *G01N 33/6872* (2013.01); *G01N 23/223* (2013.01); *G01N 33/502* (2013.01); *G01N 2223/076* (2013.01)

(58) Field of Classification Search
USPC ................................ 435/29; 436/172; 378/44
See application file for complete search history.

*Primary Examiner* — Sharmila G. Landau
*Assistant Examiner* — Paul Martin

(57) ABSTRACT

The present invention comprises a method for measuring the transport of analytes through a cell. The method comprises the steps of providing one or more cells containing at least 10 picograms of an analyte within a volume defined by the area of an x-ray excitation beam and a depth of live times the 1/e attenuation, depth for at least one characteristic x-ray signal of the analyte as attenuated by water. The method further comprises the step of removing at least a of portion of the analyte from the cells. The method also comprises the steps of exciting at least a portion of the analyte that has been removed from the cells with an x-ray beam; and using an x-ray detector to measure x-ray fluorescence.

19 Claims, 10 Drawing Sheets

US 9,063,154 B2

METHODS FOR MEASURING ANALYTE TRANSPORT ACROSS BARRIERS USING X-RAY FLUORESCENCE

RELATED APPLICATIONS/CLAIM OF PRIORITY

This Application is related to and claims priority from provisional Application Ser. No. 61/133,697, filed Jul. 1, 2008, and entitled Label Free Assay for Measuring chemical Transport Across Cell Membranes; and from provisional application Ser. No. 61/208,115, filed Feb. 20, 2009, and entitled Method and Apparatus for Measuring Transport Across Membranes; and is a continuation of the U.S. application Ser. No. 12/496,532 filed on Jul. 11, 2009; and which provisional and all of the foregoing applications are incorporated by reference herein.

GOVERNMENT RIGHTS

This invention was made with US Government support under contract number 1R43GM080781-01 awarded by the National Institute of Health. The Government has certain rights to this invention.

FIELD OF THE INVENTION

The present invention relates to a method and apparatus for measuring the rate of transport through membranes.

BACKGROUND OF THE INVENTION

The identification of potentially important drugs often requires the measurement of the effect of these drugs on the transport of ions through membranes. For example, some drugs have produced life-threatening toxicity, associated with a delay in cardiac re-polarization or QT interval prolongation related to ion movement. For example, several drugs were recently withdrawn from the market because of their effect on the cell membrane transport system.

Ion channels are ubiquitous pore-forming proteins that allow the transport of ions across cell membranes, Ion channels facilitate the movement of a particular ionic species (for example, Na+, K+, Ca2+, Cl−) between cellular compartments and/or across the outer cell membrane with varying ion selectivity. Ion channels are dynamic structures which respond to external factors such, as voltage gradients, ligands and mechanical forces. The pharmaceutical industry developed therapeutics that modify ion channel function. Examples include the anti-epileptics such as the sodium channel blocker carbamazepine, the antihypertensive dihydropyridine calcium channel blockers (NORVASC™) and sulphonylurea potassium channel openers for diabetes AMARYL™). Recent total annual sales of ion channel targeted drugs are around $20 billion.

Ion channels are difficult molecular targets for drug development. Difficulties arises from the lack of suitable high throughput screening assay formats, the complexity of ion channel biophysics, and the range of potential binding sites and binding modes for drugs.

There remains a need for simpler methods for measuring transport rates of ions through a membrane.

Therefore, an object of the present invention is to provide a method and apparatus for measuring the transport rates of ions through membranes.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

BRIEF DESCRIPTION OF INVENTION

Briefly, the present invention comprises a method for measuring the transport of an analyte from a cell. The method comprises the step of providing one or more cells which are loaded with an analyte. The analyte is then at least partially unloaded from the cells. The analyte is then measured using x-ray fluorescence.

The present invention also comprises a method for measuring the transport of an analyte into a cell. This method comprises the steps of providing one or more cells; increasing the amount of an analyte in the cells; and measuring the analyte using x-ray fluorescence.

The present invention also comprises an apparatus for measuring the transport of chemicals across cellular barriers. The apparatus comprises a chamber having an inlet, an outlet, and a means for retaining cells during exchange of the solution in the chamber. The chamber also has at least one location that is translucent to x-rays. The apparatus also comprises an X-ray fluorescence spectrometer oriented to analyze the cells through the X-ray translucent location in the chamber.

DETAILED DESCRIPTION

Briefly, the present invention relates to using x-ray fluorescence (XRF) to measure the effective rate of transport of a chemical through a membrane.

Figure 1:
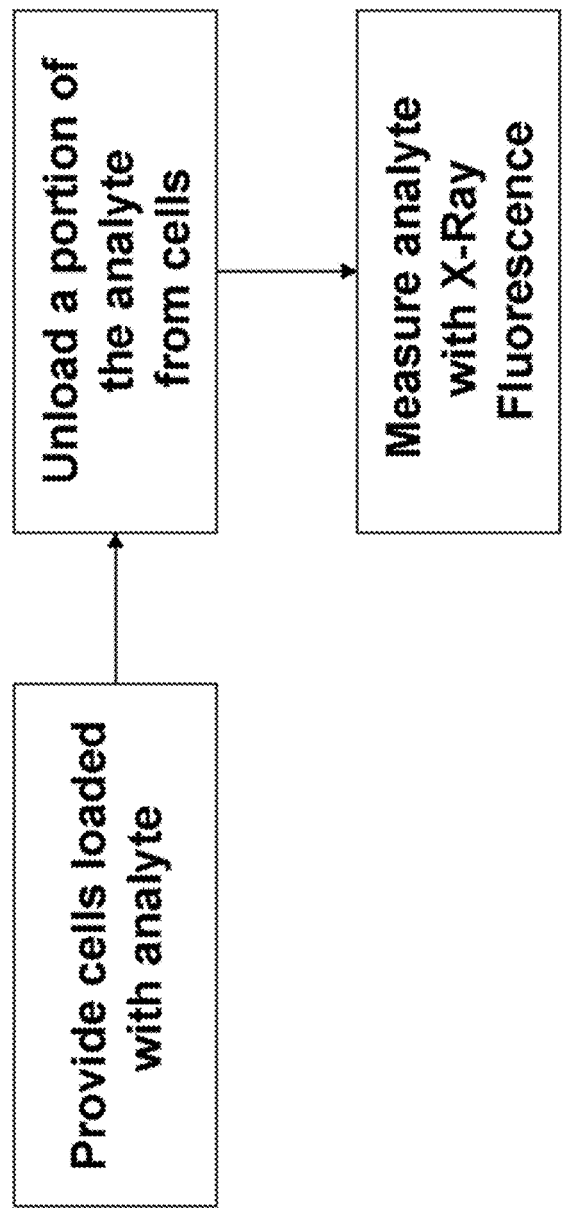
FIG. 1 shows a flowchart representation of the method of the present invention.

An embodiment of the method of the present invention is shown in FIG. 1. This embodiment comprises the steps of providing cells which are loaded with an analyte. The cells are then exposed to conditions that cause them to unload the analyte. The analyte is measured with x-ray fluorescence. Preferably, the unloaded analyte is substantially removed from the volume defined by the area of the x-ray fluorescenece excitation beam that is incident on the cells and a depth of five times the 1/e depth for at least one characteristic signal of the analyte in water.

Figure 2:
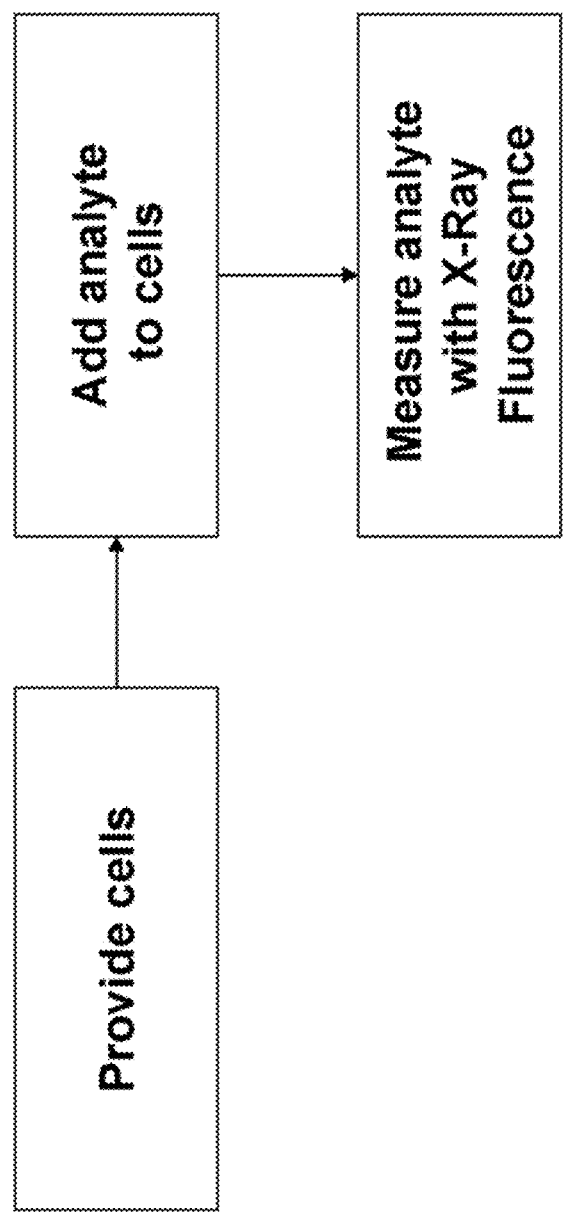
FIG. 2 shows another flowchart representation of the method of the present invention.

An alternative embodiment of the method of the present invention is shown in FIG. 2. This embodiment comprises the steps of providing cells, which are then loaded with the analyte, and measuring the analyte using x-ray fluorescence. Preferably, the before the cells are loaded, the analyte is substantially depleted in the volume defined by the area of the x-ray fluorescenece excitation beam that is incident on the cells and a depth of five times the 1/e depth for at least one characteristic signal of the analyte in water.

In both the embodiments of the method of the present invention, the characteristics of the similar components and steps are the same.

The cells are preferably living, biological cells, which preferably express ion channels. It should be understood that cells may be part of a tissue; or that the term cell may refer to subcellular components with membranes, such as mitochondria; or other subcellular components that provide restricted analyte transport such as endoplasmic reticulum, or micelles or similar. More preferably, the cells overexpress ion channels. Generally, the cells should be substantially bounded by a physical barrier, such as a membrane or a wall, which encloses a volume of material, such as the analyte, water, proteins, DNA and other biological chemicals. The physical barrier has the characteristic that it may pass the analyte at different rates when it is exposed to different stimuli. For example, the physical barrier may be a cell membrane comprising an ion channel or other membrane protein, where the ion channel passes ions at different rates in the presence of inhibitors or activators. Preferred cells are adherent. An example of a cell line that is compatible with the present invention is the hERG CHO-K1 cell line, available from CreaCell, Biopolis, 5, avenue du Grand Sablon, 38700 La Tronche, France.

Figure 5:
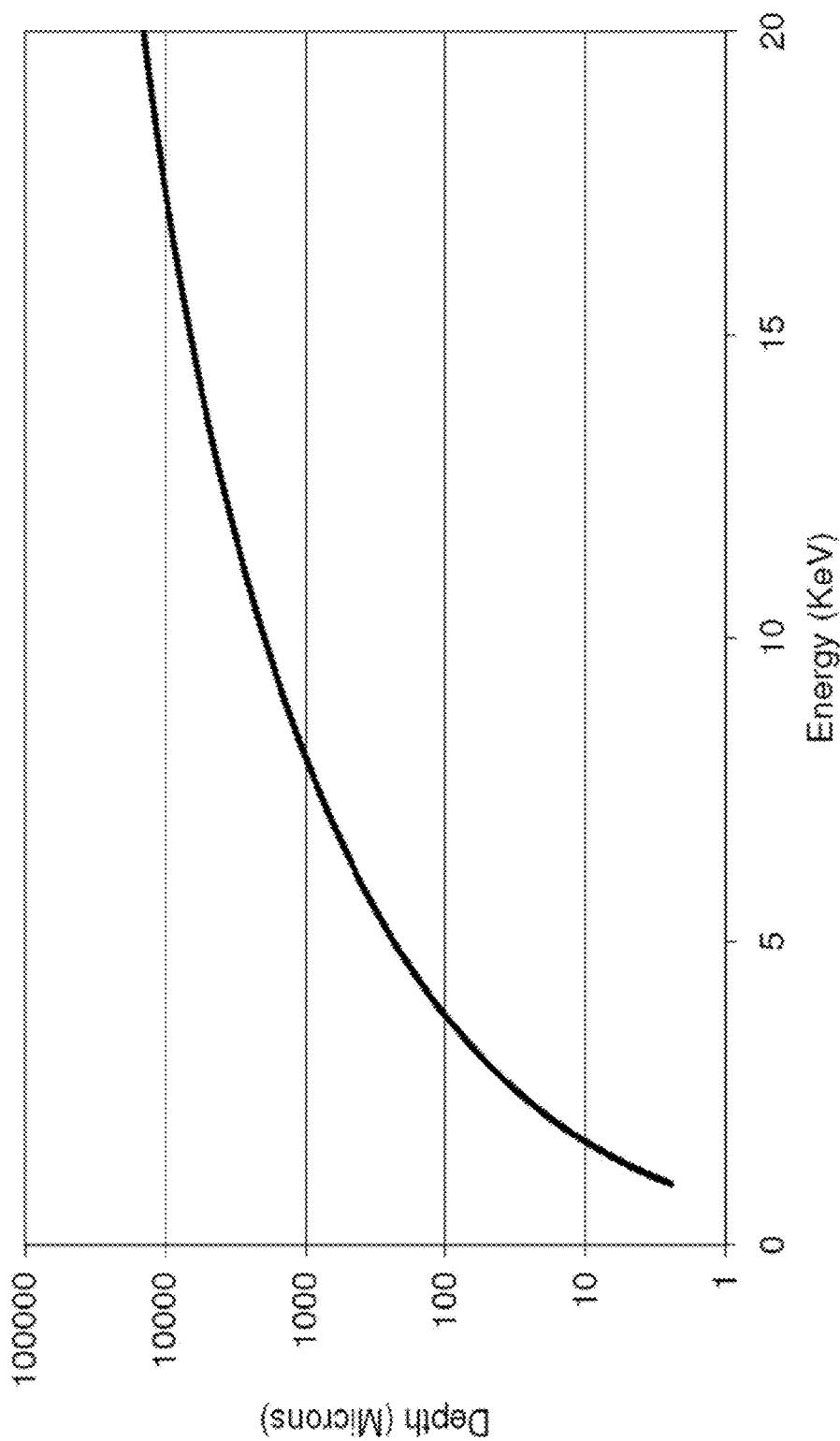
FIG. 5 shows a curve of the calculated 1/e attenuation depth for x-rays in water.

The analyte preferably comprises a chemical element having an atomic number greater than 10, and more preferably a chemical element selected from the list of zinc, cadmium, thallium, sodium, potassium, rubidium, cesium, magnesium, calcium, barium, strontium, chlorine, bromine, and iodine. More preferably, the analyte comprises a chemical element that has at least one characteristic x-ray fluorescence emission signal having an energy of 2.5 KeV or greater. The cells preferably incorporate an amount of the analyte such that a population of cells within a volume defined by the area of the x-ray excitation beam from the x-ray fluorescence instrument that is incident on the sample and a depth of five times the 1/e attenuation depth for at least one characteristic x-ray signal of the analyte as attenuated by water contains at least 10 picograms of the analyte; the 1/e depths for x-ray energies between 1 KeV and 20 KeV are shown in FIG. 5. More preferably the cells comprise, incorporate or internalize an amount of the analyte such that a population of cells within a volume defined by the area of the x-ray excitation beam from the x-ray fluorescence instrument that is incident on the sample and a depth of five times the 1/e attenuation depth contains between 10 nanomolar and 5 molar concentration of the analyte.

The cells are preferably immobilized; immobilized in this context means that a quantity of cells equivalent to at least 1% of the cells which are in the beam path of x-ray fluorescence excitation beam at the beginning of an x-ray fluorescence measurement are retained in the beam path of x-ray fluorescence excitation beam for a period of time which is greater than the measurement time of the x-ray fluorescence measurement. More preferably, immobilized in this context means that a quantity of cells equivalent to at least 1% of the cells which are in the beam path of x-ray fluorescence excitation beam at the beginning of an x-ray fluorescence measurement are retained in the beam path of x-ray fluorescence excitation beam for at least 10 seconds.

Examples of methods to immobilize the cells include the following: the cells may be immobilized by means of a filter that retains the cells and allows the first solution and second solution to pass. Preferably the cells may be immobilized by adherence to a solid support, such as foam, sheet, film, membrane, scaffold, gel, adherence factor, adherent cell line, tissue, differential diffusion rates, fluidic forces, or differentiated cell or other surface on which the cells can adhere. The cells may be adherent or be part of a tissue or other differentiated cell mass. If a foam is used, an open cell foam is preferable, and a partially reticulated open cell foam is most preferable.

The analyte may be conveniently unloaded by removing any solution in which the cells are supported, and adding a second solution. The second solution may be added after removing the first solution, for example, by pouring out the first solution or filtering the cells from the first solution, followed by adding the second solution. The second solution may alternatively be added to the first solution, so that the second solution displaces the first solution. The second solution is a convenient method to add one or more stimuli to release the analyte. The stimuli preferably comprise at least one of the materials selected from the list of a chemical that induces the analyte to traverse the physical barrier, a chemical that inhibits the analyte from traversing the physical barrier, a solvent that is substantially depleted in the analyte, a chemical that induces ion channel activity, and a chemical that inhibits ion channel activity; this inhibition of ion channel activity may be direct, for example, the inhibitor binds to the ion channel; or indirectly, for example the chemical inhibits ion channel activity by binding to an helper protein or cofactor or similar; the mechanism of the inhibition is not important for the functioning of the present invention. The first solution may conveniently be removed by displacing or diluting the first solution with the second solution. The first solution may also be removed by draining, decanting, or otherwise physically moving a substantial portion of the first solution with or without simultaneously replacing it with a second solution. If the cells are exposed to a second solution, the second solution preferably has a different composition than the first solution. The second solution preferably comprises one or more of the following chemical(s): a chemical to replace the analyte, such as replacing rubidium ions with potassium ions; a chemical to induce channel activity, such as a high concentration of potassium; and a chemical to modify ion channel activity, such as astemizole, cisapride, or terfenadine. Examples of this difference in composition may be the identity or concentration of one or more solutes, or the identity of the solvent, including mixtures of solvents. Preferably the difference between the first solution and the second solution is that the second solution is substantially depleted in the analyte. In this context, "substantially depleted" means that the concentration of the analyte in the second solution is at least ten times less than the concentration of the analyte in the cells when the cells are first exposed to the second solution. More preferably, "substantially depleted" means that the concentration of the analyte in the second solution is at least one hundred times less than the concentration of the analyte in the cells when the cells are first placed in the second solution.

The cells are analyzed by x-ray fluorescence. Examples of x-ray fluorescence spectrometers that may be conveniently used with the present invention are the EDAX Eagle XPL energy dispersive X-ray fluorescence spectrometer, equipped with a microfocus X-ray tube, a polycapillary x-ray focusing optic, lithium drifted silicon solid-state detector, processing electronics, and vendor supplied operating software; and the KEVEX™ Omicron model 952-102 with a collimated X-ray tube and a Si(Li) detector, processing electronics, and vendor supplied operating software. The x-ray fluorescence spectrometer preferably comprises a moveable stage, and more preferably a stage that may be moved in at least two dimensions, and most preferably a stage that may be moved in at least three dimensions. Preferred x-ray sources emit polychromatic x-rays, or fir which the measured spectrum of the x-ray tube or the measured spectrum of scattered x-rays from a hydrocarbon sample comprises x-rays having at least two different energies separated by at least 0.5 KeV.

The analyte is preferably measured while it is co-located with the cells because it allows real time or near real time measurements and easily analyzed analyte efflux measurement, but the analyte may be measured after the cells are lysed, after the analyte has been unloaded from the cells, or the difference between the analyte which is loaded in the cells and the amount of analyte to which the cells have been exposed may be measured. Removing or reducing the matrix, such as by lysing the cells or drying the cells can produce superior measurement limits.

This embodiment of the method of the present invention may readily be multiplexed.

Multiple measurements may be obtained over a period of time or with different first solutions or second solutions. This allows kinetic parameters to be calculated and inhibition constants such as an $IC_{50}$ to be calculated.

Figure 3:
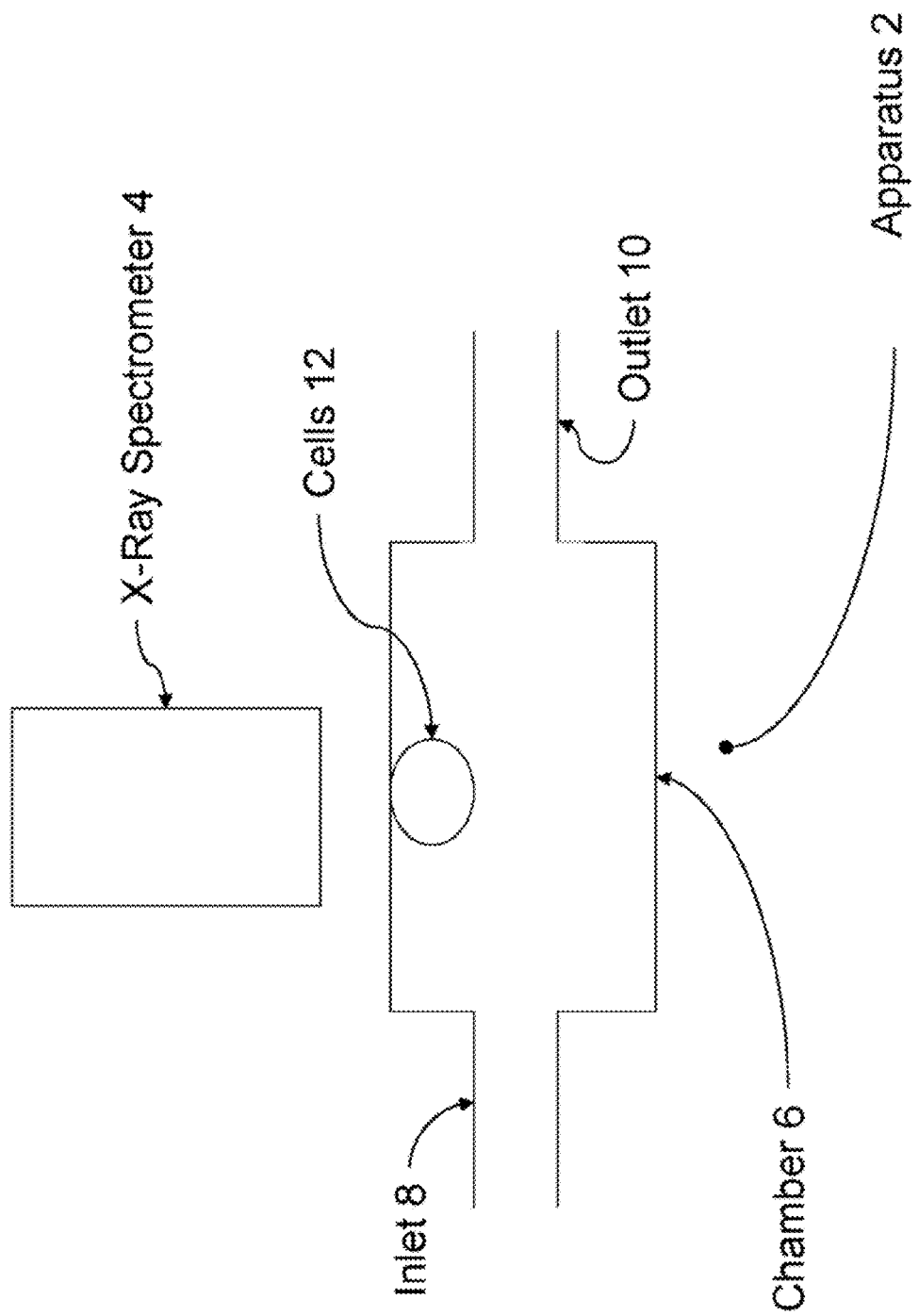
FIG. 3 shows schematic representation of the apparatus of the present invention.

An embodiment of the apparatus of the present invention is shown in FIG. 3. Apparatus 2 comprises X-Ray Fluorescence Spectrometer 4, which is oriented to analyze Cells 12 in Chamber 6. Chamber 6 comprises an Inlet 8 and an Outlet 10. Chamber 6 also comprises either a filter to retain Cells 12 or a surface upon which cells can adhere or another means to retain Cells 12; if a foam is used, the foam is preferably an open cell or partially reticulated foam; preferably, the means of retaining Cells 12 is sufficient to retain Cells 12 during an exchange of a solution that substantially surrounds Cells 12. The means for retaining Cells 12 is preferably one or more surfaces to which an adherence cell may adhere. At least one portion of Chamber 6 must be translucent or transparent to x-rays. Chamber 6 may be a discrete unit, or it may be a portion of a conduit which retains cells.

Cells 12 should have a physical barrier, such as a membrane or a wall, which substantially encloses a volume of material, such as an analyte, water, proteins, DNA and other biological chemicals. The physical barrier has the characteristic that it may pass the analyte at different rates when it is exposed to different stimuli. For example, the physical barrier may be a cell membrane with a plurality of ion channels, where the plurality of ion channels pass ions at different rates in the presence of inhibitors or activators. Preferred cells are adherent.

X-Ray Fluorescence Spectrometer 4 comprises an x-ray excitation source and an x-ray detector. Examples of x-ray fluorescence spectrometers that may be used with the present invention are the EDAX Eagle XPL energy dispersive X-ray fluorescence spectrometer, equipped with a microfocus X-ray tube, a polycapillary x-ray focusing optic, lithium drifted silicon solid-state detector, processing electronics, and vendor supplied operating software; and the KEVEX™ Omicron model 952-102 with a collimated X-ray tube and a Si(Li) detector, processing electronics, and vendor supplied operating software. The x-ray fluorescence spectrometer preferably comprises a moveable stage, and more preferably a stage that may be moved in at least two dimensions, and most preferably a stage that may be moved in at least three dimensions. Preferred x-ray sources emit polychromatic x-rays, or for which the measured spectrum of the x-ray tube or the measured spectrum of scattered x-rays from a hydrocarbon sample comprises x-rays having at least two different energies separated by at least 0.5 KeV.

The portion of Chamber 6 that is translucent or transparent to x-rays has the characteristic that the X-ray translucent location passes at least 0.1% of the highest energy x-ray fluorescence signal that are emitted by the portion of the analyte that is located within 1 micron of the x-ray translucent location and that are normal to the x-ray translucent location and incident upon the x-ray translucent location.

Chamber 6 preferably does not leach the analyte, and more preferably does not comprise the analyte, and most preferably does not comprise the same element as the element in the analyte that is being measured using x-ray fluorescence. Chamber 6 is preferably biologically compatible, so that at least the surfaces of Chamber 6 that contact the first solution or second solution are not toxic to cells; in this context, not toxic to cells means that the surface of Chamber 6 does not kill more than 50% of the cells within 30 minutes. Chamber 6 also optionally allows cells to adhere to at least one of its inner surfaces; this inner surface may be a foam inside Chamber 6.

The means for retaining Cells 12 may be either a filter (i.e. a component that retains the cells and allows the solution to pass) or a surface to which the cells may adhere. An example of a filter is a regenerated cellulose filter. Preferably, the means for retaining Cells 12 is a surface to which adherent cells may adhere. If a surface to which cells may adhere is used; examples of surfaces are polystyrene, polycarbonate, and polyurethane; the examples of the surface are sheets, films foams, and other shapes. The surfaces are optionally treated with chemicals to promote cell adherence, for example, by treatment with collagen-I or poly-1-lysine or etching. The means for retaining Cells 12 preferably is disposed such that the Cells 12 which are in the volume defined by the area of the x-ray excitation beam from the x-ray fluorescence instrument that is incident on the sample and a depth of five times the 1/e attenuation depth for at least one characteristic x-ray signal of the analyte as attenuated by water contains at least 10 picograms of the analyte; the 1/e depths for x-ray energies between 1 KeV and 20 KeV are shown in FIG. 5. More preferably the means for retaining Cells 12 is disposed such that the Cells 12 which are in the volume defined by the area of the x-ray excitation beam from the x-ray fluorescence instrument that is incident on the sample and a depth of five times the 1/e attenuation depth for at least one characteristic x-ray signal of the analyte as attenuated by water contains between 10 nanomolar and 5 molar concentration of the analyte.

Optionally, and preferably, Apparatus 2 further comprises flow controls to modify a solution entering the chamber. This flow control could comprise a pump which is capably of providing a solution with a gradient of concentrations of different solutes or solvents.

This embodiment of the apparatus of the present invention may readily be multiplexed, for example by etching or engraving multiple copies of Apparatus 2 in a single block of plastic or by attaching multiple individual Apparatuses 2 together.

Figure 4:
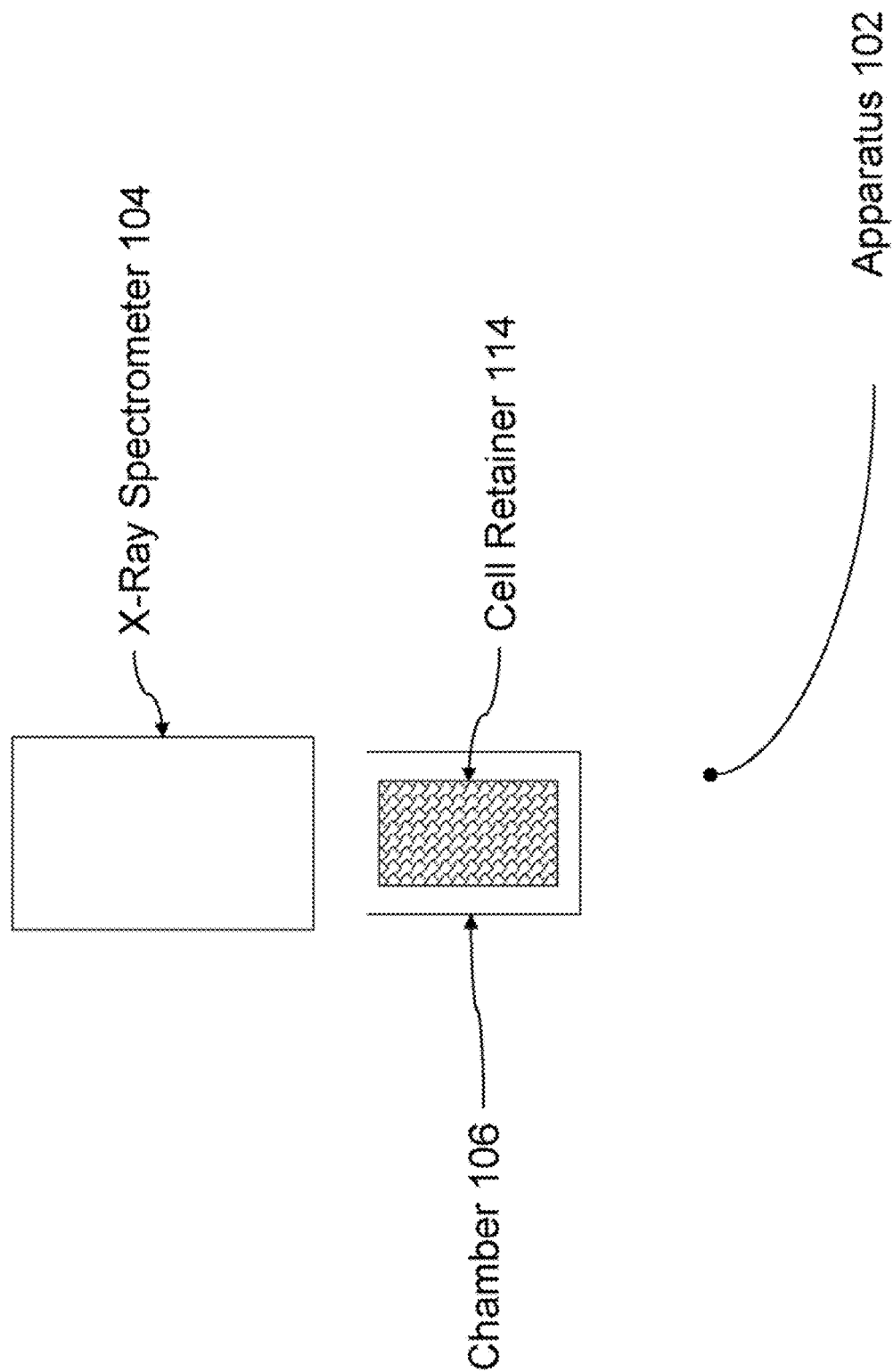
FIG. 4 shows another schematic representation of the apparatus of the present invention.

Another embodiment of the apparatus of the present invention is shown in FIG. 4. Apparatus 102 comprises X-Ray Fluorescence Spectrometer 104 disposed to analyze cells in Chamber 106; although X-Ray Fluorescence Spectrometer 104 is shown measuring the cells through an opening in Chamber 106, it should be understood that X-Ray Fluorescence Spectrometer 104 may be disposed in any direction that allows it to measure the cells, e.g. measuring the cells through the bottom surface of Chamber 106 is acceptable if that surface is translucent to x-rays. Chamber 106 also optionally comprises either a filter to retain the Cells 112 and/or a surface upon which cells can adhere, shown schematically as Cell Retainer 114. Cell Retainer 114 may be a foam, a structured surface, a gel, tissue sample, or other means for retaining Cells 112. Alternatively, the cells may be allowed to settle e.g. using gravity or centrifugation or reduced pressure through a filter, or other means for separating the cells from the solution. At least one portion of Chamber 106 must be translucent or transparent to x-rays; this translucent or transparent portion of Chamber 106 may be an opening in Chamber 106. Chamber 106 may be a discrete unit, or it may be part of a multiplexed unit containing multiple copies of Chamber 106.

The orientation of Chamber 106 and the x-ray excitation beam and the x-ray detector must allow at least a portion of the population of cells to occupy the volume defined by the intersection of the x-ray excitation beam path and the viewable volume of the x-ray detector. Preferably the orientation of Chamber 106 and the x-ray excitation beam and the x-ray detector must allow at least a portion of the population of cells comprising at least 100 picograms of the analyte to occupy the volume defined by the intersection of the x-ray excitation beam path and the viewable volume of the x-ray detector. More preferably the orientation of Chamber 106 and the x-ray excitation beam and the x-ray detector must allow at least a portion of the population of cells comprising at least 100 picograms of the analyte to occupy the volume defined by the intersection of the x-ray excitation beam path and the viewable volume of the x-ray detector, and any barrier between the cells and the x-ray fluorescence detector attenuates the portion of the highest energy x-ray fluorescence signal and that is emitted normal to the barrier by the analyte that is located within 5 microns of the barrier by less than about 99.9% or allows at least 0.1% of the highest energy x-ray fluorescence signal from analyte to pass.

X-Ray Fluorescence Spectrometer 104 comprises an x-ray excitation source and an x-ray detector. Examples of x-ray fluorescence spectrometers that may be used with the present invention are the EDAX Eagle XPL energy dispersive X-ray fluorescence spectrometer, equipped with a microfocus X-ray tube, a polycapillary x-ray focusing optic, lithium drifted silicon solid-state detector, processing electronics, and vendor supplied operating software; and the KEVEX™ Omicron model 952-102 with a collimated X-ray tube and a Si(Li) detector, processing electronics, and vendor supplied operating software. The x-ray fluorescence spectrometer preferably comprises a moveable stage, and more preferably a stage that may be moved in at least two dimensions, and most preferably a stage that may be moved in at least three dimensions. Preferred x-ray sources emit polychromatic x-rays, or for which the measured spectrum of the x-ray tube or the measured spectrum of scattered x-rays from a hydrocarbon sample comprises x-rays having at least two different energies separated by at least 0.5 KeV.

This embodiment of the apparatus of the present invention may readily be multiplexed, for example by etching or engraving multiple copies of Apparatus 102 in a single block of plastic or by attaching multiple individual Apparatuses 102 together.

EXAMPLE 1

Human-ether-a-go-go expressing Chinese Hamster Ovary Cells (hERG CHO-K1) obtained from CreaCell, Biopolis 5, Avenue du Grand Sablon, 38700 La Tronche, FRANCE, were grown in T150 flasks at 37° C. under 5% carbon dioxide in growth media consisting of F-12 Nutrient mixture (HAM, obtained from Invitrogen, part number 21765-029), 10% Foetal Bovine Serum (FBS), antibiotic-antimycotic (10,000 units penicillin, 10,000 ug streptomycin, 25 ug amphotericin B/mL, obtained from Invitrogen, part number 15240-062), and 1.2 mg/ml geneticin (obtained from Invitrogen, part number 10131-027). When cells reached approximately 80% confluency, the cells were trypsinized (using Trypsin-EDTA) and counted (using a hemacytometer). Cells were resuspended in growth media at a concentration of $0.1 \times 10^6$ cells in 300 microliters of growth media. 300 microliters of cell suspension were transferred to polyurethane foam (PUF) (30 ppi, partially reticulated, from McMaster-Carr part number 86225K11 cut into one-quarter inch diameter discs) pretreated with 10 micrograms type 1 collagen from calf skin (obtained from Sigma, part number C8919) per $cm^2$ of PUF in a 48-well plate. Individual PUFs were incubated at 37° C. at 5% carbon dioxide for approximately 24 hours at which time they were transferred to a 60 millimeter diameter petri dish and covered with growth media and incubated at 37° C. at 5% carbon dioxide until approximately 80% confluent. Individual PUFs were then rinsed three times in Rb-/K-buffer consisting of 0.22 um filtered, pH 7.4 aqueous buffer containing 155.4 mM sodium chloride, 2 mM calcium chloride, 0.8 mM sodium dihydrogen phosphate, 1 mM magnesium chloride, 5 mM glucose, and 25 mM HEPES buffer.

Figure 6:
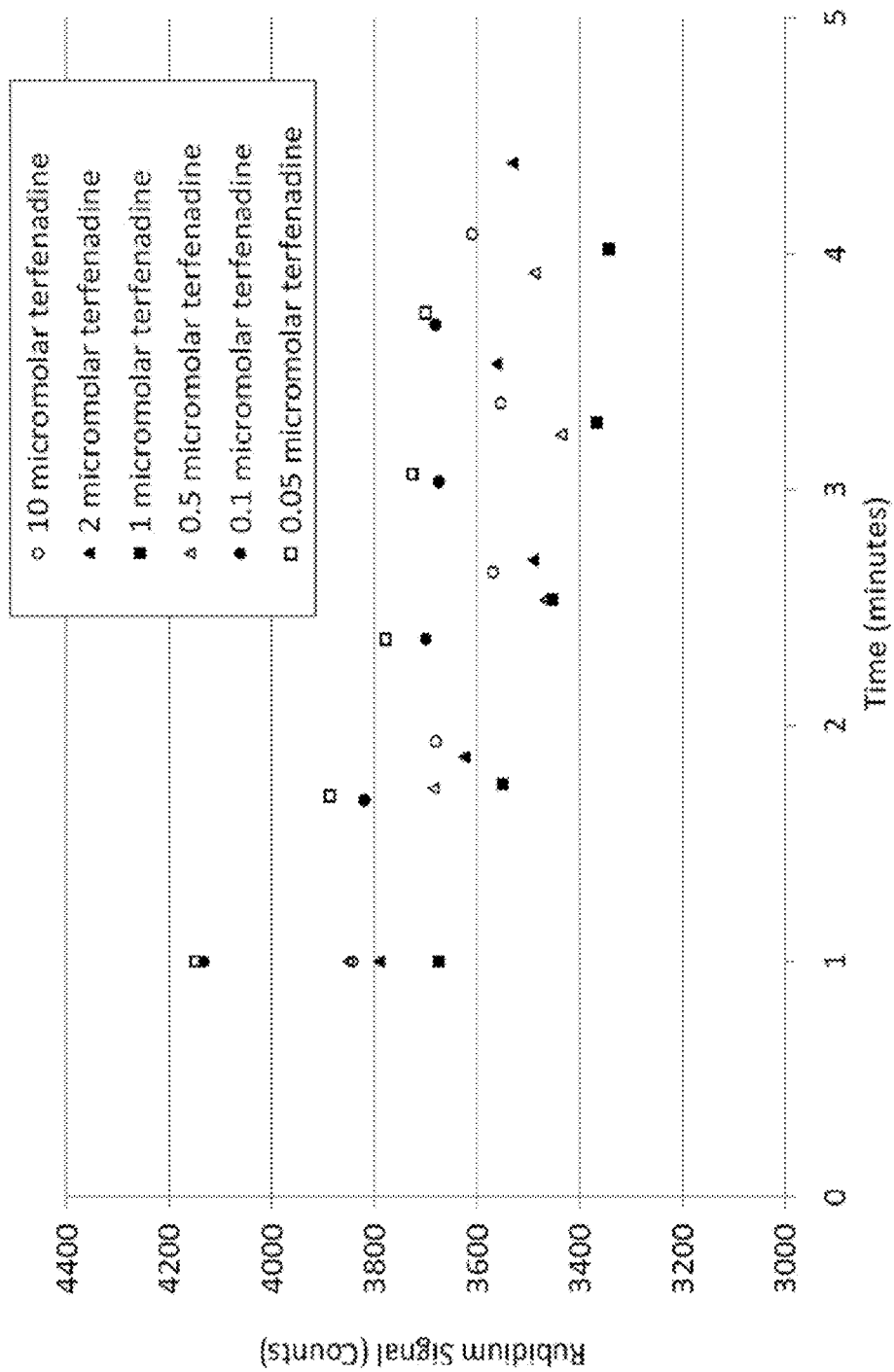
FIG. 6 shows a set of rubidium efflux rate data.

PUFs were loaded with Rb ions via a three hour incubation at 37° C. at 5% carbon dioxide in 8 mL Rb+ Loading Buffer consisting of 0.22 um filtered, pH 7.4 aqueous buffer containing 5.4 mM rubidium chloride, 150 mM sodium chloride, 2 mM calcium chloride, 0.8 mM sodium dihydrogen phosphate, 1 mM magnesium chloride, 5 mM glucose, and 25 mM HEPES buffer. PUFs were treated with channel inhibitors by incubating in varying concentration terfenadine in dimethyl sulfoxide (DMSO) for 30 minutes at 37° C. at 5% carbon dioxide, as shown in FIG. 6. Individual PUFs were then rinsed three times in Rb-/K-buffer consisting of 0.22 um filtered, pH 7.4 aqueous buffer containing 155.4 mM sodium chloride, 2 mM calcium chloride, 0.8 mM sodium dihydrogen phosphate, 1 mM magnesium chloride, 5 mM glucose, and 25 mM HEPES buffer.

Figure 8:
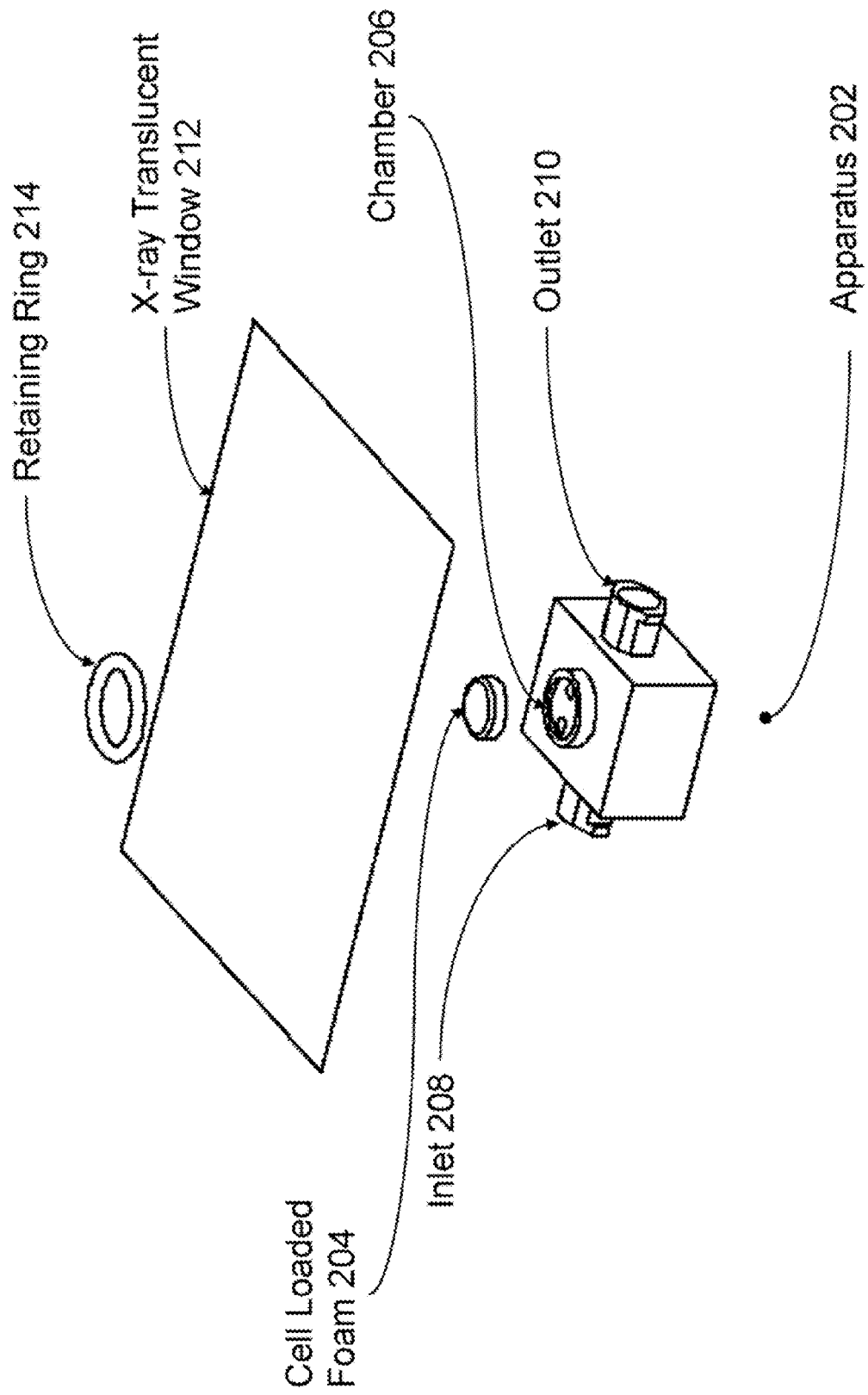
FIG. 8 shows a schematic of an apparatus of the present invention.
Figure 9:
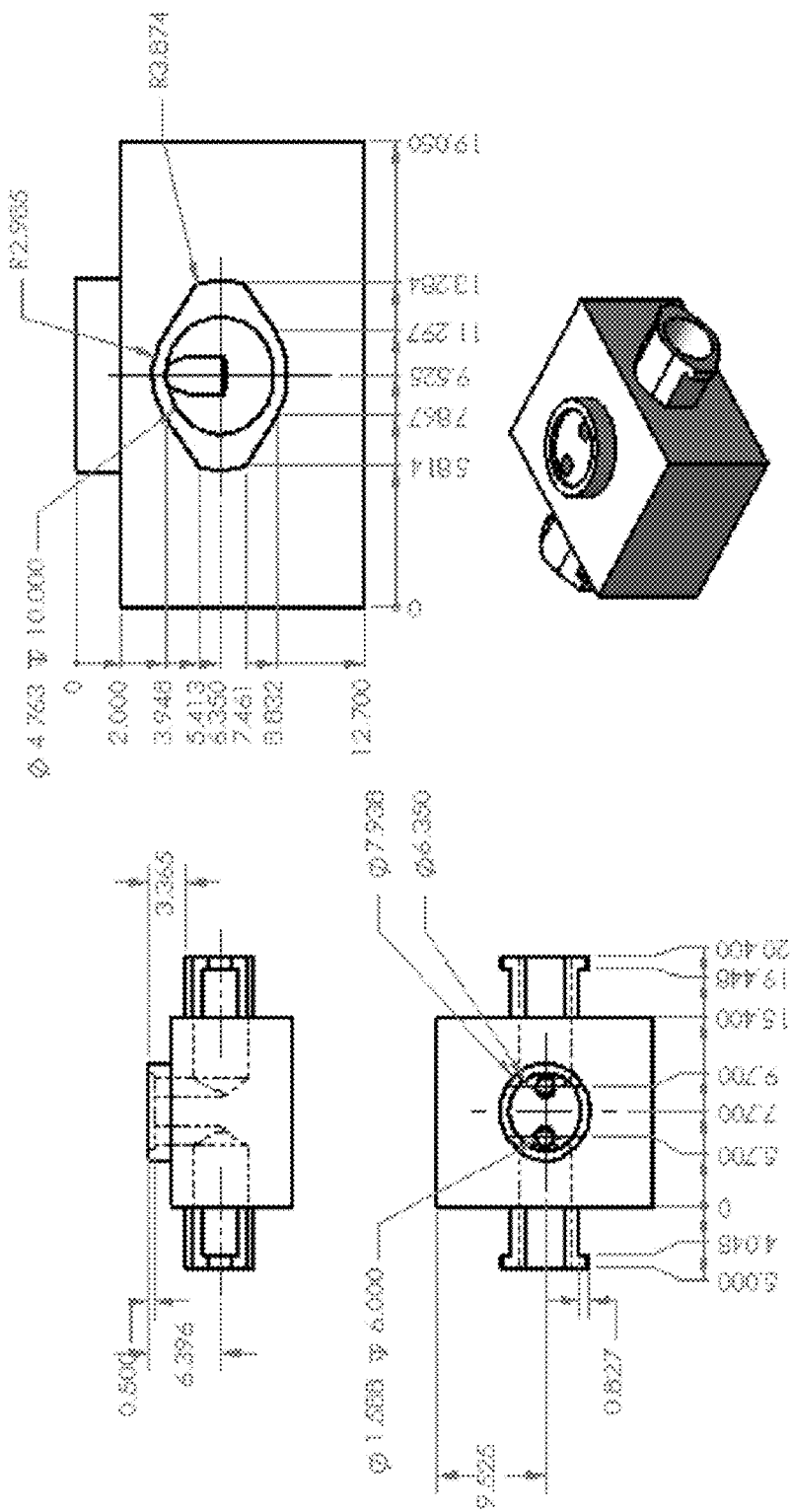
FIG. 9 shows a schematic of an apparatus of the present invention.
Figure 10:
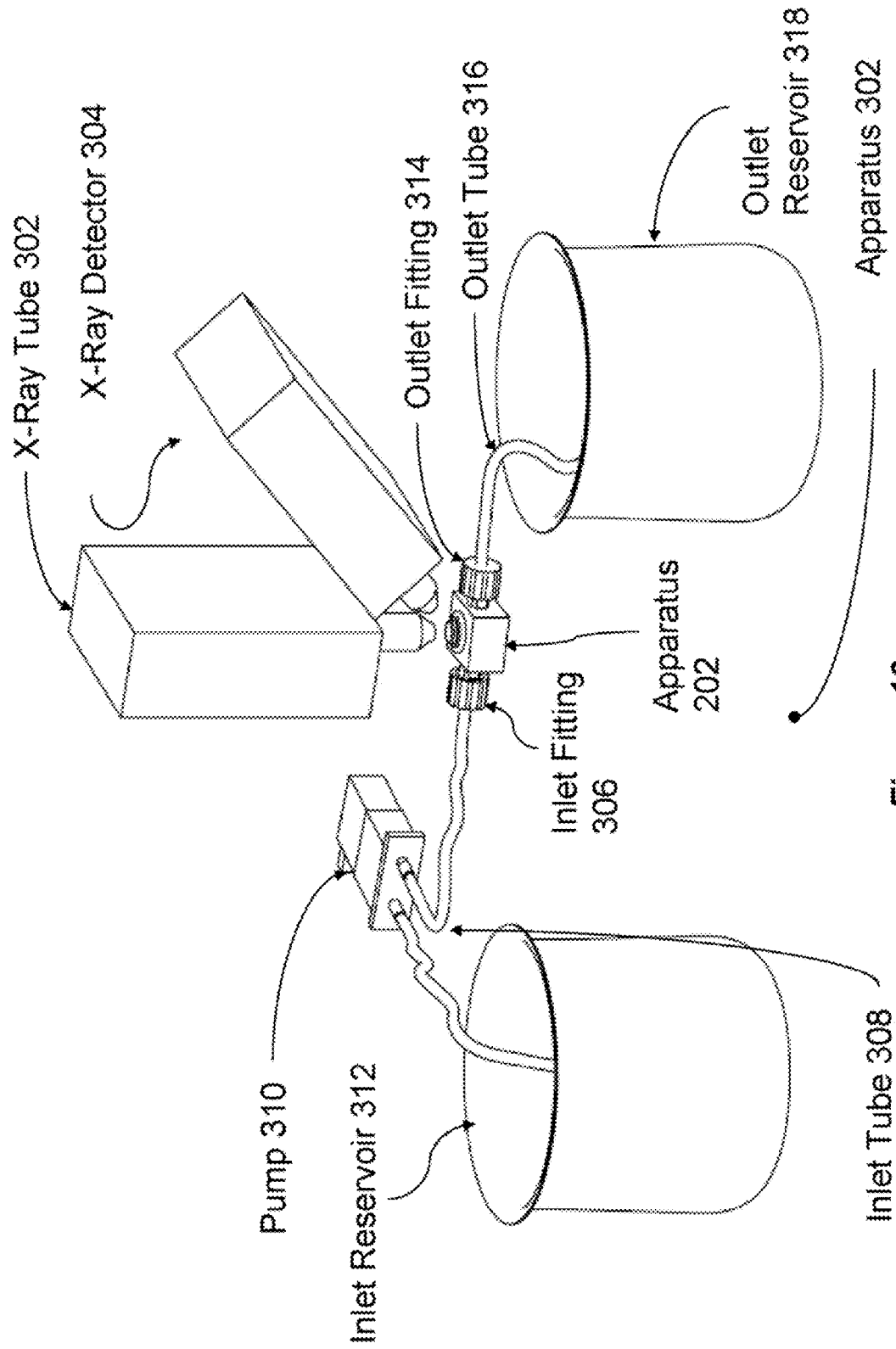
FIG. 10 shows a schematic of an apparatus of the present invention.

Three individual PUFs were then inverted and stacked in Apparatus 202 as shown in FIG. 8. FIG. 8 shows Apparatus 202, which comprises Chamber 206, Inlet 208 that allows liquid to enter Chamber 206, and Outlet 210 which allows liquid to exit from Chamber 206. Cell Loaded Foam 204 comprised set of three foam PUFs loaded with CHO-K1 cells loaded with rubidium as described above. Cell Loaded Foam 204 was placed in Chamber 206. A sheet of ULTRALENE™ (X-Ray Translucent Window 212) and an o-ring (Retaining Ring 214) were used to seal Chamber 206. FIG. 8 does not show the x-ray fluorescent spectrometer or the fluid control system. FIG. 9 shows a schematic of Apparatus 202, excluding the Cell Loaded Foam 204, the X-Ray Translucent Window 212, and the Retaining Ring 214. FIG. 10 shows a schematic of Apparatus 302, which comprises Apparatus 202, Apparatus 302 comprises X-Ray Tube 302 and X-Ray Detector 304, which are disposed to analyze the cells in Apparatus 202. Apparatus 302 also shows the inlet fluidics, comprising Inlet Fitting 306 which attaches Inlet Tube 308 to Apparatus 202, and Pump 310 which pumps liquid from Inlet Reservoir 312 through Inlet Tube 308 to Apparatus 202. Apparatus 302 also comprises outlet fluidics, comprising Outlet Fitting 314 which connects Apparatus 202 to Outlet Tube 316. Outlet Tube 316 allows liquid to exit Apparatus 202 and reach Outlet Reservoir 318.

Figure 7:
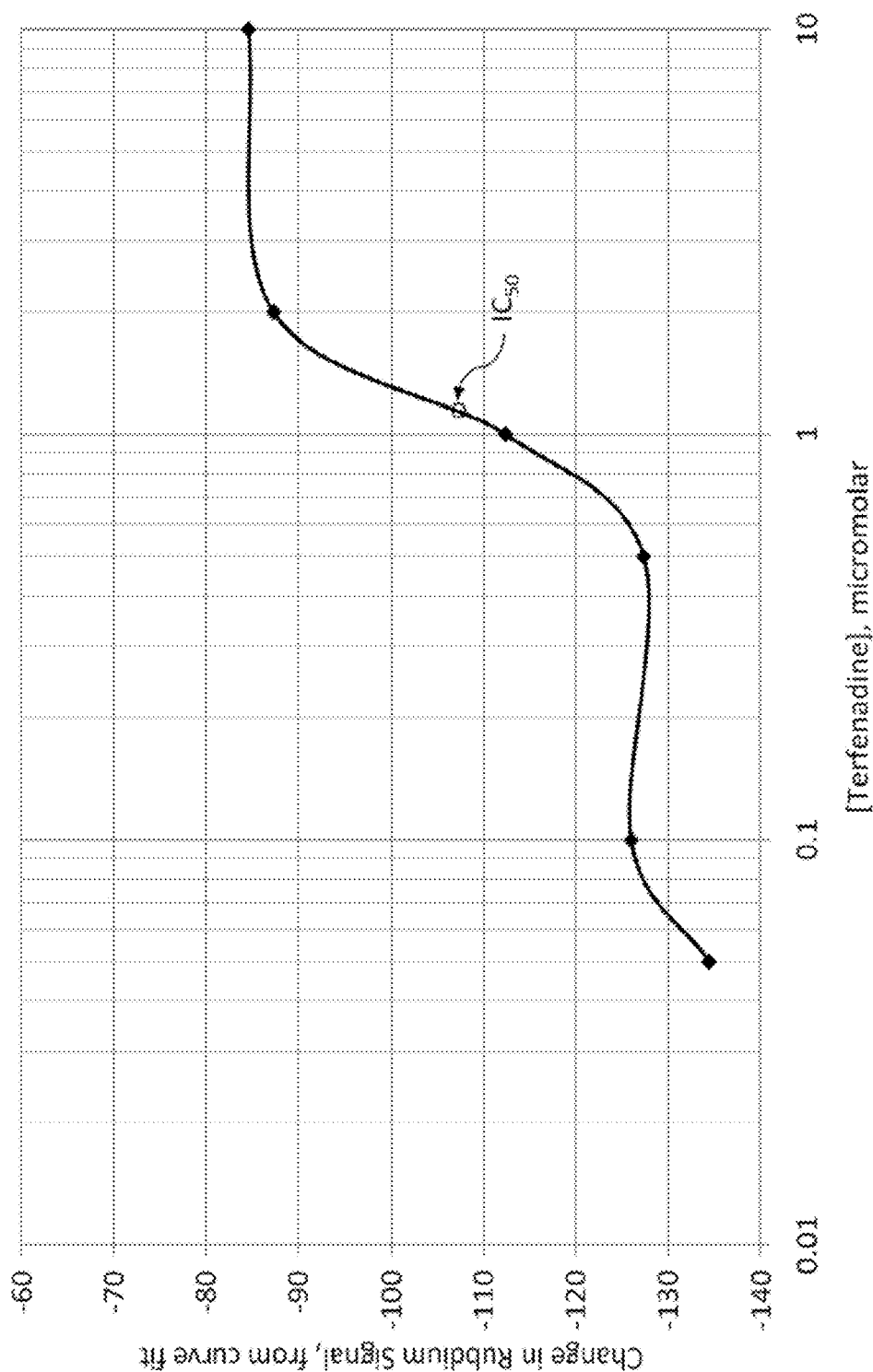
FIG. 7 shows a plot of rubidium efflux rates versus inhibitor concentration.

The inlet line was then purged with 50 mM K Flow Buffer consisting of 0.22 um filtered, pH 7.4 aqueous buffer containing 50 mM potassium chloride, 150 mM sodium chloride, 2 mM calcium chloride, 0.8 mM sodium dihydrogen phosphate, 1 mM magnesium chloride, 5 mM glucose, and 25 mM HEPES buffer. The inlet line was then connected to the flow device inlet. A static x-ray fluorescence reading was taken using an x-ray fluorescence spectrometer equipped with a Rh x-ray tube run at 25 kV and 0.1 mA, lithium-drifted silicon detector, 1 mm collimator; after which the flow buffer pump was started. Subsequent x-ray fluorescence readings were taken under flow conditions over a period of time. Then entire set of flow data for varying inhibitor concentrations was then compiled, and plotted as shown in FIG. 6. The rates of rubidium efflux were found by fitting each set of efflux data shown in FIG. 6. The efflux rates, which describe the loss of rubidium signal, were then plotted versus the concentration of added terfenadine, to obtain an IC50, as shown in FIG. 7.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring the transport of an analyte from a cell, comprising the steps of providing one or more cells wherein the cells comprise at least 10 picograms of an analyte within a volume defined by the area of an x-ray, excitation beam and a depth of five times the 1/e attenuation depth for at least one characteristic x-ray signal of the analyte as attenuated by water; removing at least a of portion of the analyte from the cells; exciting at least a portion of the analyte that has been removed from the cells with an x-ray beam; and using an x-ray detector to measure x-ray fluorescence.

2. The method of claim 1, wherein the one or more cells comprise an enclosed volume substantially bounded by a physical barrier; the enclosed volume being capable of comprising the analyte, and the analyte being capable of traversing the physical barrier, the rate of the traversing being controlled by one or more stimuli.

3. The method of claim 1, wherein the analyte comprises an element having a characteristic x-ray fluorescence signal having an energy greater than about 2.5 KeV.

4. The method of claim 1, wherein the stimuli comprise at least one of the materials selected from the list of; a chemical that induces the analyte to traverse the physical barrier, a chemical that inhibits the analyte from traversing the physical barrier, a solvent that is substantially depleted in the analyte, a chemical that induces ion channel activity, and a chemical that inhibits ion channel activity.

5. The method of claim 1, wherein the cells are retained in the beam path by means of one or more of the mechanisms selected from a scaffold, gel, foam, adherence factor, adherent cell line, tissue, differential diffusion rates, or fluidic forces.

6. The method of claim 1, wherein at least a portion of the cells are living immediately prior to an x-ray fluorescence measurement.

7. The method of claim 1, wherein at least a portion of the cells are living after an x-ray fluorescence measurement.

8. A method for measuring the transport of an analyte from a cell, comprising the steps of providing one or more cells, wherein the cells comprise an analyte having a concentration of between 10 nanomolar and 5 molar within a volume defined by the area of the x-ray excitation beam from the x-ray fluorescence instrument that is incident on the sample and a depth of five times the 1/e attenuation depth; removing at least a of portion of the analyte from the cells; exciting at least a portion of the analyte that has been removed from the cells with an x-ray beam; and using an x-ray detector to measure x-ray fluorescence.

9. The method of claim 8, wherein, the cells comprise at least 100 picograms of the analyte within the volume defined by the intersection of the x-ray excitation beam path and the viewable volume of the x-ray detector.

10. The method of claim 8, wherein the x-ray beam is polychromatic.

11. The method of claim 8, wherein the cells are provided in contact with a solution.

12. The method of claim 8, wherein at least a portion of the cells are living immediately prior to an x-ray fluorescence measurement.

13. The method of claim 8, wherein at least a portion of the cells are living after an x-ray fluorescence measurement.

14. A method for measuring the transport of an analyte from a cell, comprising the steps of providing one or more cells, wherein the cells comprise an analyte; exciting the cells using x-rays; and using an x-ray detector to measure a first x-ray fluorescence measurement; removing at least a or portion of the analyte from the cells; exciting at least a portion of the analyte that has been removed from the cells with an x-ray beam; and using an x-ray detector to measure x-ray fluorescence.

15. The method of claim 14, wherein the x-rays are polychromatic.

16. The method of claim 14, wherein at least a portion of the cells are living between the first x-ray fluorescence measurement and the second x-ray fluorescence measurement.

17. The method of claim 14, wherein the x-rays are provided in a beam, and wherein the cells comprise an analyte having a concentration of between 10 nanomolar and 5 molar within a volume defined by the area of the x-ray excitation beam from the x-ray fluorescence instrument that is incident on the sample and a depth of five times the 1/e attenuation depth at the time of the first x-ray fluorescence measurement.

18. The method of claim 14, wherein the cells are provided in contact with a solution.

19. The method of claim 14, wherein the cells comprise at least 100 picograms of the analyte within the volume defined by the intersection of the x-ray excitation beam path and the viewable volume of the x-ray detector at the time of the first x-ray fluorescence measurement.

* * * * *